United States Patent
Dimmock et al.

(10) Patent No.: US 7,582,655 B2
(45) Date of Patent: Sep. 1, 2009

(54) ANTINEOPLASTIC COMPOUNDS

(75) Inventors: Jonathan R. Dimmock, Saskatoon (CA); Umashankar Das, Saskatoon (CA)

(73) Assignee: University of Saskatchewan, Saskatoon, Saskatchewan (CA)

( * ) Notice: Subject to any disclaimer, the term of this patent is extended or adjusted under 35 U.S.C. 154(b) by 0 days.

(21) Appl. No.: 11/562,675

(22) Filed: Nov. 22, 2006

(65) Prior Publication Data
US 2007/0155733 A1    Jul. 5, 2007

Related U.S. Application Data

(60) Provisional application No. 60/738,568, filed on Nov. 22, 2005.

(51) Int. Cl.
   C07D 211/82    (2006.01)
   A61K 31/45     (2006.01)
   A61K 31/4545   (2006.01)
   A61K 31/4523   (2006.01)

(52) U.S. Cl. .................... 514/327; 514/237.2; 514/316; 544/130; 546/188; 546/221

(58) Field of Classification Search ................. 514/390, 514/327, 316, 237.2; 544/130; 546/221, 546/188
See application file for complete search history.

(56) References Cited

U.S. PATENT DOCUMENTS

| | | | |
|---|---|---|---|
| 3,852,279 A | | 12/1974 | Krapcho et al. |
| 4,415,621 A * | | 11/1983 | Specht et al. ................ 428/172 |
| 4,946,960 A * | | 8/1990 | Wade et al. ................. 548/150 |
| 5,217,846 A | | 6/1993 | Smothers |
| 6,664,272 B2 * | | 12/2003 | Snyder et al. ............... 514/327 |

FOREIGN PATENT DOCUMENTS

| | | | |
|---|---|---|---|
| JP | 59084936 A * | 5/1984 | |
| JP | 60131539 A * | 7/1985 | |
| JP | 10198055 A * | 7/1998 | |

OTHER PUBLICATIONS

Huni, Albrecht; Frank, Friedel "Bile pigments. XXXVII. Oxidation of pyrrole with hydrogen peroxide." Z. physiol. Chem., 282, 96-103 1947 (abstract only).*
McElvain, S. M.; McMahon, Robert E. "Piperidine derivatives. XXI. 4-Piperidone, 4-piperidinol, and certain of their derivatives." Journal of the American Chemical Society, 1949, 71, 901-6.*
Buu-Hoi, N. P.; Roussel, Odette; "Condensation of aromatic and heterocyclic aldehydes with g-piperidones; relation between structure and choleretic activity of the products of this reaction." Jacquignon, Pierre (C.N.R.S., Gif-sur-Yvette). Bulletin de la Societe Chimique de France 1964, 12, 3096-9 (abstract only).*
Richter, P "Synthesis of antiproteolytically active 3,5-bis(4-amidinobenzyl)- and 3,5-bis(4-amidinobenzylidene)-4-piperidone derivatives." Pharmazie, 1980, 35(2), 75-7 (abstract only).*
Rovnyak, George "Tricyclic thiazolo[3,2-a]thiapyrano[4,3-d]pyrimidines and related analogs as potential antiinflammatory agents" Journal of Heterocyclic Chemistry, 1981,18(2), 327-31.*
David R. Lide, ed., CRC Handbook of Chemistry and Physics, 88th Edition (Internet Version 2008), "http://www.hbcpnetbase.com" CRC Press/Taylor and Francis, Boca Raton, FL. "Definitions of Scientific Terms" "aryl groups" Section 2, p. 30.*
"Aryl" Hawley's Condensed Chemical Dictionary, 14th Edition Hawley's Condensed Chemical Dictionary, 14th Edition, 2002, Wiley online.*
"Aryl" General Chemistry Glossary, online "http://antoine.frostburg.edu/cgi-bin/senese/searchglossary.cgi?query=aryl&shtml=%2Fchem".*
A. D. McNaught and A. Wilkinson "Compendium of Chemical Terminology" "aryl group", The Gold Book, Second Edition "http://old.iupac.org/publications/compendium/index.html" Blackwell Science, 1997.*
Dimmock, J. R.; "Cytotoxic Evaluation of Some 3,5-diarylidene-4-piperidones and Various Related Quaternary Ammonium Compounds and Analogs." Journal of Pharmaceutical Sciences, 1994, 83(8), 1124-30 (abstract only).*
Artico, Marino "Geometrically and ConformationallyRestrained Cinnamoyl Compounds as Inhibitors of HIV-1 Integrase", Journal of Medicinal Chemistry 1998, 41(21), 3948-3960.*

(Continued)

Primary Examiner—Rita J Desai
Assistant Examiner—David K O'Dell
(74) Attorney, Agent, or Firm—Gail C. Silver; Borden Ladner Gervais LLP (57) ABSTRACT

The present invention relates to 4-piperidone derivatives represented by the following formula (I) and the acid addition salts thereof.

(I)

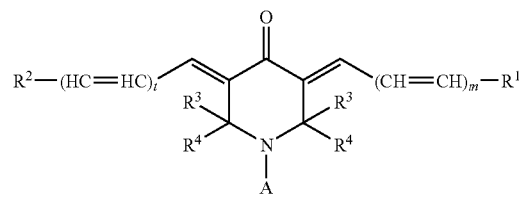

The method of preparation and antineoplastic activity of the said compounds are disclosed. A number of the compounds possess submicromolar $IC_{50}$ and $CC_{50}$ values and have a selective toxicity for colon cancers and leukemic cells. In addition, many of the compounds are able to reverse multidrug resistance.

16 Claims, 1 Drawing Sheet

OTHER PUBLICATIONS

Li, et. al. "1-Benzyl-5-(1-naphthylmethylene)piperidinespiro-3,3'-1'-methyl-4'-(1-naphthyl)pyrrolidinespiro-2',3"-indole-2",4-dione-diethyl ether" (1/0.75). Acta Crystallographica, Section E: Structure Reports Online, E59(7), o1025-o1027 (abstract).*

Ulrich Jacquemard, "Synthesis of 3,5-bis(2-indolyl)pyridine and 3-[(2-indolyl)-5-phenyl]- pyridine derivatives as CDK inhibitors and cytotoxic agents" Bioorganic & Medicinal Chemistry 16 (2008) 4932-4953.*

Cenzo Congiu "Design, synthesis, and in vitro antitumor activity of new 1,4-diarylimidazole-2-ones and their 2-thione analogues" Bioorganic & Medicinal Chemistry Letters 18 (2008) 989-993.*

Pozharskii et. al. Heterocycles in Life and Society Wiley, 1997, pp. 1-6.*

Das et. al. "Design, synthesis and cytotoxic properties of novel 1-[4-(2-alkylaminoethoxy)phenylcarbonyl]-3,5-bis(arylidene)-4-piperidones and related compounds" European Journal of Medicinal Chemistry 2007, 42, 71-80.*

Wolff, M.E. Burger's Medicinal Chemistry 4th Ed. Part I, Wiley: New York, 1979, 336-337.*

Das, et al., "Design, synthesis and cytoxic properties of novel 1-[4-(2-alkylaminoethoxy)phenylcarbonyl]-3,5-bis(arylidene)-4-piperidones and related compounds", European Journal of Medicinal Chemistry, 2006.

Krapcho et al., "Bicyclic Pyrazolines, Potential Central Nervous System Depressants and Antiinflammatory Agents", Journal of Medicinal Chemistry, 1979, vol. 22, No. 2, pp. 207-210.

Dimmock et al., "3,5-Bis(Phenylmethylene)-1-(N-arylmaleamoyl)-4-piperidones: A Novel Group of Cytotoxic Agents", Journal of Enzyme Inhibition and Medicinal Chemistry, Aug. 2003, vol. 18 (4), pp. 325-332.

Dimmock et al., "Cytotoxic N-[4-(3-aryl-3-oxo-1-propenyl)phenylcarbonyl]-3,5-bis(phenylmethylene)-4-piperidones and related compounds", European Journal of Medicinal Chemistry, 2002, vol. 37, pp. 961-972.

Dimmock et al., "Cytotoxic Evaluation of Some N-Acyl and N-Acyloxy Analogues of 3,5-Bis(Arylidene)-4-Piperidones", Drug Design Discovery, 1994, vol. 12, pp. 19-28.

Dimmock et al., "Bioactivities of Chalcones", Current Medicinal Chemistry, 1999, vol. 6, pp. 1125-1149.

Dimmock et al., "The reaction of some nuclear substituted acyclic conjugated styryl ketones and related Mannich bases with ethanethiol", Canadian Journal Chemistry, 1980, vol. 58, pp. 984-991.

Dimmock et al., "Evaluation of Nuclear-Substituted Styryl Ketones and Related Compounds for Antitumor and Cytotoxic Properties", Journal of Pharmaceutical Sciences, Feb. 1975, vol. 64, No. 2, pp. 241-249.

Dimmock et al., "A Conformational and Structure-Activity Relashionship Study of Cytotoxic 3,5Bis(arylidene)-4-piperidones and Related N-Acryloyl Analogues", Journal of Medicinal Chemistry, 2001, vol. 44, No. 4, pp. 586-593.

Dimmock et al., "Conformational and Quantitative Structure-Activity Relationship Study of Cytotoxic 2-Arylidenebenzocycloalkanones", Journal of Medicinal Chemistry, 1999, vol. 42, No. 8, pp. 1358-1366.

Dimmock et al., "3,5-Bis-Benzylidene-4-Piperidones and Related Compounds With High Activity Towards P388 Leukemia Cells", Drug, Design and Delivery, 1990, vol. 6, pp. 183-194.

Dimmock et al., "Evaluation of Some N-Acyl Analogues of 3,5-Bis(Arylidene)-4-Piperidones For Cytotoxic Activity", Drug Design and Discovery, 1992, vol. 8, pp. 291-299.

Dimmock et al., "Cytoxic Evaluation of Some 3,5-Diarylidene-4-piperidones and Various Related Quaternary Ammonium Compounds and Analogs", Journal of Pharmaceutical Sciences, vol. 83, No. 8, Aug. 1994, pp. 1124-1130.

Dimmock et al., "Cytoxic Mannich Bases of 1-Arylidene-2tetralones", "Journal of Enzyme Inhibition and Medicinal Chemistry", Aug. 2003, vol. 18 (4), pp. 313-324.

Buu-Hoi et al., "La condensation des aldehydes aromatiques et heterocycliques avec les y-piperidones; relation entre structure et activite choleretique chez les produits de cette reaction", Bulletin de la Societe Chimique de France, vol. 12, 1964, pp. 3096-3099 (relevant to compounds 3,9-11).

Jha et al., "3,5-Bis(arylmethylene)-4-piperidone derivatives as novel anticancer agents", Indian Journal of Chemistry, vol. 45B, Oct. 2006, pp. 2313-2320.

Jha et al., "Syntheses of 4-(3,5-Bisphenylmethylene-4-oxo-piperidin-1-yl)-4-oxo-but-2Z-enoic Acid Arylamides as Candidate Cytoxic Agents", Synthetic Communications, vol. 33, No. 7, 2003, pp. 1211-1223.

Kuettel et al., "Piperidine Derivatives, XI, 3-Carbethoxy-4-Piperidone and 4-piperidone Hydrochloride", Journal of American Chemical Society, vol. 53, Jul. 1931, pp. 2692-2696.

El-Subbagh, et al., "Synthesis and Biological evaluation of certain A,-unsaturated ketones and their corresponding fused pyridines as antiviral and cytoxic agents", Journal of Med. Chem., vol. 43, 2000, pp. 2915-2921.

PCT Patent Application No. PCT/CA2006/001908 International Preliminary Report on Patentability dated Jun. 5, 2008.

* cited by examiner

Figure 1

ANTINEOPLASTIC COMPOUNDS

PRIORITY

The present invention claims priority from U.S. Provisional Patent Application Ser. No. 60/738,568 filed on 22 Nov. 2005, which is incorporated herein by reference.

FIELD OF INVENTION

The present invention relates to 4-piperidone derivatives possessing antineoplastic activities and their use in the treatment of cancer.

BACKGROUND OF THE INVENTION

A number of α,β-unsaturated ketones display cytotoxic and anticancer properties (Dimmock et al, Curr. Med. Chem. 1999, 6, 1125-1149; Dimmock et al, J. Med Chem 1999, 42, 1358-1366) and are believed to interact with cellular thiols with little or no affinity for hydroxyl and amino groups in nucleic acids (Mutus et al, Anal Biochem, 1989, 177, 237-243; Baluja et al Chem Ind. 1964, 2053-2054). This characteristic provides the potential to develop these compounds as cytotoxics, bereft of the genotoxic properties present in certain antineoplastic agents (Bevenuto et al, J. Pharm. Sci. 1993, 82, 988-991). The Mannich base form of such compounds has been investigated. For instance, Mannich bases of some conjugated enones have been shown to lead to significant increase in both the rate of thiolation and alkylation (Dimmock et al, Can J. Chem 1980, 58, 984-991) and cytotoxicity (Dimmock et al, J Pharm Sci 1975, 64, 241-249). However, compounds, such as the conjugated arylidene ketone of Formula (A) shown below, are toxic to mice.

$R^1=R^2=H$, Cl, $NO_2$, $N(CH_3)_2$, alkoxy or alkyl;
$R^3=H$ or alkyl

Related cyclic analogues of Formula (B), shown above, have been prepared to reduce the toxicity of compounds of Formula (A).

Compound B1 (Formula B with $R^1=R^2=H$) is a cyclic Mannich base of a dienone and possesses cytotoxic activity towards the murine lymphocytic leukemia P388/MRI cell line and does bind to a synthetic DNA, poly(d(AT)); more surprisingly, five consecutive daily doses of 240 mg/kg did not induce fatalities in mice (Dimmock et al., Drug Des Delivery 1990, 6, 183-194).

Various N-substituted derivatives of compound B1 have been prepared and tested: N-3-carboxy-2-propenoyl derivatives of compound B1 were evaluated against P388/MRI cells (Dimmock et al, Drug Des. Deliv. 1990, 6, 183-194). N-Acyl derivatives (Dimmock et al, Drug Des Discovery 1992, 10, 291-299), N-amidic, and N-carbamate derivatives (Dimmock et al, Drug. Des. Discovery 1994, 12, 19-28) of compound B1 were screened against murine L1210 cells and a panel of human tumours. N-acryloyl amides (Dimmock et al, J. Med. Chem 2001, 44, 586-593), N-amidic derivatives (shown as Formula C below) (Dimmock et al. Eur J. Med. Chem., 2002, 37, 961-972), and N-maleamoyl derivatives (Dimmock et al, J. Enz. Inhib. Med. Chem., 2003, 18, 325-332) of compound B1 were evaluated against murine P388 and L1210, human Molt 4/C8 and CEM T-lymphocytes.

Compounds of Formula C have been shown to inhibit human N-myristoyltransferase and fyn kinase.

Nearly 50 percent of human cancers are either completely resistant to chemotherapy or respond only transiently, after which they are no longer affected by commonly used anti-cancer drugs. This phenomenon is referred to as multidrug resistance (MDR) and is inherently expressed by some tumour types while others acquire MDR after exposure to chemotherapy treatment. The ability of a therapeutic to dampen or eliminate MDR in a cell is thus an important consideration.

SUMMARY OF THE INVENTION

In one aspect, the present invention provides novel antineoplastic compounds, structurally divergent from currently available anticancer drugs. This structural divergence may provide compounds devoid of cross resistance to contemporary medications including the antineoplastic alkylating agents. The synthesis of new compounds is disclosed herein, together with experiments demonstrating their activity in cytotoxicity ($IC_{50}$ and $CC_{50}$) assays against cancer cell lines. The compounds are also useful in reversing MDR (multidrug resistance).

Thus, in one aspect, the present invention provides a 4-piperidone compound represented by structural formula (I):

wherein $R^1$ and $R^2$ independently represent alkyl, alkoxy, aryl, or heteroaryl; $R^3$ and $R^4$ independently represent H, alkyl, hydroxyalkyl, or carboxylate ester; m and t independently represent an integer from 0 to 3; A represents H or A', where A' represents wherein n represent an integer from 0 to 4 and indicates the number of substituents on the benzene ring, o represent an integer from 0 to 4; X represents $(CH_2)_r$, CO, COO, SO, $SO_2$, or O, where r represents an integer from 0 to 4; Y represents O, S, NH, N(alkyl), N(aryl), or $(CH_2)_s$, where s represents an integer from 0 to 4; Z represents H, $N(alkyl)_2$, NH(alkyl), $N(aryl)_2$, NH(aryl), alkyl, substituted alkyl, $+N(alkyl)_3$, or where B represents O, S, $(CH_2)_q$, NH, N-alkyl, or N-aryl and p and q independently represent an integer from 0 to 4; or a pharmaceutically acceptable salt thereof, with the proviso that the free base and the hydrochloride salt of compounds 1a, 1b, and 1c are excluded.

In another aspect, the present invention provides a method of preparing the compounds of the invention, comprising the steps of: reacting a compound of formula (IV)

with a compound of formula T-A' (V), where T represents a halogen, and A' represents in the presence of a base.

Formula (I) and Formula (IV) each contain two $R^3$ substituents, which are the same or different, and are as defined herein. Formula (I) and Formula (IV) each contain two $R^4$ substituents, which are the same or different, and are as defined herein.

In another aspect, the present invention provides uses of the compounds and pharmaceutical compositions thereof for treating cancer and for reversing multidrug resistance.

DETAILED DESCRIPTION OF THE INVENTION

Chemistry

Compounds of the invention include compounds of Formula (I).

Preferably, the alkyl or alkoxy groups are substituted or unsubstituted, branched or unbranched C1-C7, preferably C1-5. Preferred alkyl groups are methyl or ethyl. Preferred alkoxy groups are methoxy and ethoxy. Possible substituents are known in the art and include halogen, alkoxy, alkyl, phenyl, and/or nitro groups. Halogen may be fluorine, chlorine, bromine, or iodine, and preferably fluorine or chlorine.

Preferably $R^1$ and $R^2$ are the same or different substituted or unsubstituted, branched or unbranched alkyl, aryl, or heteroaryl groups, wherein the alkyl group is preferably as defined above. Aryl groups are preferably substituted or unsubstituted phenyl rings in which substitutions are preferably independently placed in the 2, 3, or 4 positions of the phenyl ring, or combined at 3,4; 2,4; 2,3; 2,5; 2,6; 3,5; 3,6; 4,6; 3,4,5; 2,4,6; or 2,3,4 positions. Substituents may include halogen, alkoxy, alkyl, phenyl, nitro, and phosphonate groups. Phosphonate groups include $—P(O)(OH)_2$, $—P(O)(OH)(O\text{-alkyl})$, $—P(O)(O\text{-alkyl})_2$, $—P(O)(OH)(O\text{-aryl})$, $—P(O)(O\text{-aryl})_2$. Preferred substituents are 4-fluoro, 4-chloro, 4-methoxy, 4-nitro, 4-methyl, 3,4-dimethoxy, 3,4-dichloro, 3,4,5-trimethoxy and 2,4,6-trimethoxy. $R^1$ and $R^2$ may desirably be any one of phenyl, 4-chlorophenyl, 4-nitrophenyl, and/or 4-methylphenyl. The heteroaryl groups are preferably 2, 3, or 4-pyridyl, 2-thienyl or 2-furyl. Both m and t may independently be any integer from 0 to 3. In one aspect, m and t are both 0.

$R^3$ or $R^4$ may independently be H, alkyl, or carboxylate ester. Each $R^3$ may be the same or different. Each $R^4$ may be the same or different. The alkyl group is preferably as defined above. The carboxylate ester includes alkyl carboxylates and is preferably methyl or ethyl carboxylate. In one aspect, $R^3$ and $R^4$ are both H.

Compounds referred to herein include: when A is H, $R^3=R^4=H$, and m and t are 0 in Formula (I): $R^1=R^2=$Phenyl (1a); $R^1=R^2=$4-Chlorophenyl (1b); and $R^1=R^2=$4-Nitrophenyl (1c).

Compounds of the invention include, but are not limited to the following:

i) when A is H, $R^3=R^4=H$, and m and t are 0 in Formula (I):
$R^1=R^2=$4-Methylphenyl (1d)

(ii) when A is A' and Y $(CH_2)_oZ$ is placed at the 4-position of the benzene ring and $R^3=H$, $R^4=H$, X=CO; m and t=0; n=1; Y=O; o=2 in Formula (I):
$R^1=R^2=$Phenyl; $Z=N(CH_3)_2$ (3a)
$R^1=R^2=$4-Chlorophenyl; $Z=N(CH_3)_2$ (3b)
$R^1=R^2=$4-Nitrophenyl; $Z=N(CH_3)_2$ (3c)
$R^1=R^2=$4-Methylphenyl; $Z=N(CH_3)_2$ (3d)
$R^1=R^2=$Phenyl; $Z=N(C_2H_5)_2$ (4a)
$R^1=R^2=$4-Chlorophenyl; $Z=N(C_2H_5)_2$ (4b)
$R^1=R^2=$4-Nitrophenyl; $Z=N(C_2H_5)_2$ (4c)
$R^1=R^2=$4-Methylphenyl; $Z=N(C_2H_5)_2$ (4d)
$R^1=R^2=$Phenyl; Z=1-piperidyl (5a)
$R^1=R^2=$4-Chlorophenyl; Z=1-piperidyl (5b)
$R^1=R^2=$4-Nitrophenyl; Z=1-piperidyl (5c)
$R^1=R^2=$4-Methylphenyl; Z=1-piperidyl (5d)

$R^1=R^2=$Phenyl; Z=4-morpholinyl (6a)
$R^1=R^2=$4-Chlorophenyl; Z=4-morpholinyl (6b)
$R^1=R^2=$4-Nitrophenyl; Z=4-morpholinyl (6c)
$R^1=R^2=$4-Methylphenyl; Z=4-morpholinyl (6d)
$R^1=R^2=$Phenyl; $Z=+N(CH_3)(C_2H_5)_2I^-$ (7a)
$R^1=R^2=$4-Chlorophenyl; $Z=+N(CH_3)(C_2H_5)_2I^-$ (7b)
$R^1=R^2=$4-Nitrophenyl; $Z=+N(CH_3)(C_2H_5)_2I^-$ (7c)
$R^1=R^2=$4-Methylphenyl; $Z=+N(CH_3)(C_2H_5)_2I^-$ (7d)

(iii) when A is H, $R^3=R^4=$H, and m and t are 0 in Formula (I):
$R^1=R^2=$2-Thienyl (8a)

(iv) when A is A' and Y $(CH_2)_oZ$ is placed at the 4-position of the benzene ring and $R^3=$H, $R^4=$H, X=CO; m and t=0; n=1; Y=O; o=2 in Formula (I):
$R^1=R^2=$2-Thienyl; $Z=N(C_2H_5)_2$ (9a)

(v) when A is A' and Y $(CH_2)_oZ$ is H, and m and t are 0 in Formula (I):
$R^1=R^2=$Phenyl; $R^3=R^4=$H, X=CO; n=1 (2a)

(vi) when A is A' and Y $(CH_2)_oZ$ is placed at the 4-position of the benzene ring and $R^3=R^4=$H, X=CO; n=1; Y=O; o=0; and m and t are 0 in Formula (I):
$R^1=R^2=$Phenyl; $Z=CH_3$ (2b)

The compounds of formula (I) include acid addition salts thereof. By "acid addition salts" it is meant any salt which may be formed for the purpose of isolation, purification, and storage, such as the oxalate salt, and pharmaceutically acceptable salts meant for administration of the compound to a host, such the hydrochloride, sulfate, acetate, and citrate.

Preparation

A compound of formula (I) can be prepared according to the following reaction step:

where A represents A', whose meaning is the same as discussed earlier. T represents halogen that has the same meaning as discussed earlier.

A compound of formula (I) can be obtained by reacting compound (IV) with (V) in the presence of a base in an inert solvent. The bases used may be inorganic bases such as potassium carbonate, sodium carbonate or secondary amines such as piperidine, pyrrolidine, morpholine or tertiary amines such as triethylamine, metal hydrides such as sodium hydride and the like may be used in an amount of 1-5 equivalents. The solvent can, for example, be a polar aprotic solvent (for example, tetrahydrofuran, acetonitrile) or a halogenated hydrocarbon (for example, chloroform, dichloromethane, 1,2-dichloroethane), which solvents may be used alone or in combination. The reaction is carried out at a temperature between −10° C. and the boiling point of the solvent employed in the reaction, and is completed in 0.5 to 24 hrs.

The starting compound (IV) can be prepared according to the literature procedure (Dimmock et al, J. Med. Chem, 2001, 44, 586-593). The substituents on (IV) can be any of those mentioned for Formula (I). The starting compound (V) can be prepared according to the process described in the literature (Jones et al, J. Med. Chem. 1984, 27, 1057-1066). The intermediates and the desired compounds in the processes described above can be isolated and purified by purification methods conventionally used in organic synthetic chemistry, for example, filtration, extraction, washing, drying, concentration, recrystallization and various types of chromatography. The intermediates may also be subjected to a subsequent reaction without isolation.

The acid addition salts of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which were used to prepare the pharmaceutically acceptable acid addition salts of the base compounds of this invention are those which form non-toxic acid addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts. In the case where a quaternised salt of compound (I) is desired, compound (I) in the form of a free base is dissolved in a suitable solvent followed by addition of an alkyl halide to form a salt. The reaction is carried out at a temperature between 0° C. and the boiling temperature of the solvent employed in the reaction and is completed in 0.5 to 24 hrs.

Compound (I) and the acid addition salts thereof may be in the form of adducts with water or various solvents, which are also within the scope of the present invention.

Biological Activity

The compounds of the invention may be used to treat cancer, particularly colon cancer and leukemia. In addition, the compounds demonstrate anti-multidrug resistance properties.

Compounds of the invention (compounds 1-7) were evaluated for their cytotoxicity towards human transformed cells by treating them with human Molt 4/C8 and CEM T-lymphocytes. In addition, they were evaluated for their ability to inhibit the growth of murine L1210 cells, an ability of many clinically useful anticancer drugs. The results are shown as $IC_{50}$(micromolar) in Table 1. $IC_{50}$(micromolar) indicates the concentration of a compound which is required to inhibit the growth of the cells by 50%. The results are compared to compound 10 and to melphalan. Melphalan is an anticancer drug that exerts its effect by alkylating cellular constituents. In almost all the cases, the compounds of the invention were more potent than melphalan in both the Molt 4/C8 and the CEM assays.

A number of compounds of the invention were further assessed against numerous human malignant cell lines. An average of 49 cell lines from nine different neoplastic diseases, namely leukemia, melanoma, non-small cell lung, colon, central nervous system, ovarian, renal, prostate, and breast cancers were employed. Against most of the cell lines, compounds tested had average $IC_{50}$ values lower than those of melphalan, as shown in Table 2. For instance, 6b and 6d possess in excess of 48 and 38 times, respectively, the potency of melphalan. In particular, the $IC_{50}$s were lower towards colon and leukemic neoplasms.

An important feature of novel antineoplastic agents is the display of greater toxicity for malignant cells rather than for the corresponding normal tissues. A differentiation in cytotoxicity toward the cell lines would reveal that the compound displayed selective toxicity in contrast to being a general biocidal agent; such selectivity may translate into a preferential lethality for tumour cells rather than related non-malignant cells. Accordingly, a selective index (SI) figure for each compound was calculated as the ratio of the $IC_{50}$ values between the cell line which is the most sensitive and the cell line which is least sensitive to the compound (also shown in Table 2). The amides 3b, 4a, 6a, 6b, 6d and 7d were more selective than melphalan, in particular, 4a, 6b and 6d.

Mean $IC_{50}$ graphs were calculated as described previously (M. R. Grever, S. A. Schepartz, B. A. Chabner, Semin. Oncol. 19 (1992) 622-638). A review of the mean graphs revealed that in general the $IC_{50}$ values of the compounds were lower towards colon and leukemic neoplasms than the other cell lines. The selective toxicity for these groups of cancers is revealed in Table 2 since the $IC_{50}$ figures of many of the colon and leukemic cell lines were lower than the values for all cell lines. An effective drug against colon tumours is 5-fluorouracil. The data in Table 2 reveal that the $IC_{50}$ figures for the compounds prepared in this study towards the six colon cancer cell lines indicated in Table 2 were lower than that of 5-fluorouracil in 67% of the cases. Melphalan is used in combination chemotherapy to treat chronic leukemias and in 80% of the comparisons made for the K-562, RPMI-8226, HL-60 (TB) and SR cell lines, the compounds in series 1, 3-7 had lower $IC_{50}$ figures than melphalan. A general conclusion to be drawn from the evaluation of representative compounds against a panel of approximately 49 human tumour cell lines is that their potencies are substantially greater than certain clinically used drugs and that they have a particular toxicity towards colon cancer and leukemic cells.

In addition, the compounds were evaluated against human squamous cell carcinomas (HSC-2 and HSC-4) and human promyelocytic leukemia neoplasms (HL-60) and compared with normal cells, i.e. human gingival fibroblasts (HGF), human pulp cells (HPC) and human periodontal ligament fibroblasts (HPLF). The $CC_{50}$ values towards these three cell lines are also indicated in Table 3. $CC_{50}$(micromolar) indicates the concentration of a compound which is required to kill 50% of the cells. These data are presented in Table 3. Most of the compounds have $CC_{50}$ values less than 10 micromolar and the average $CC_{50}$ values for 3c, 4c, 5c, and 6c are submicromolar. Furthermore, almost all of the compounds in series 1 and 3 to 7 have lower average $CC_{50}$ values than the established anticancer drug melphalan.

Further evaluation of the compounds was done to determine whether they had the capacity to reverse multidrug resistance (MDR) and/or display selective toxicity to malignant cells. All of the compounds in series 1 and 3-7 were examined for their ability to reverse MDR using murine L-5178 lymphoma cells. The assay to determine MDR reversal employed murine L-5178 lymphoma cells transfected with the human MDR1 gene. The concentrations of rhodamine 123 were measured in treated and untreated transfected and parental cells and the ratios of the fluorescence intensities are referred to as fluorescence activity ratio (FAR) values. Since MDR is due, inter alia, to an increase in the efflux of a compound from cells, a FAR value of greater than 1 indicates that reversal of MDR has taken place. These data are also presented in Table 3. MDR-reversal was displayed by all of the compounds in series 3 to 6. Huge FAR values were obtained for many of the compounds using a concentration of 4 μg/ml. In contrast to a concentration of 10 micrograms/ml of a reference drug verapamil, the FAR values of the compounds of the invention ranged from 8 to 32 times that of verapamil.

Compounds which reverse MDR and exert an antineoplastic effect may be classified as bi-modal. They are superior to those compounds which have only one of these effects. The compounds of the invention can be used as either antineoplastics, MDR revertants, or for both effects.

Administration

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous), topical or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in a conventional manner.

The compounds of the invention can also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

The compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in a powder form for reconstitution with a suitable vehicle, e.g., sterile pyrogen-free water, before use.

The compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution, dry powder formulation or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, heptafluoroalkanes, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

The compounds of the invention including pharmaceutically acceptable salts and solvates thereof may be used on their own but will generally be administered in the form of a pharmaceutical composition in which the compound (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on the total composition.

Experimental

Synthesis

Figure 1:
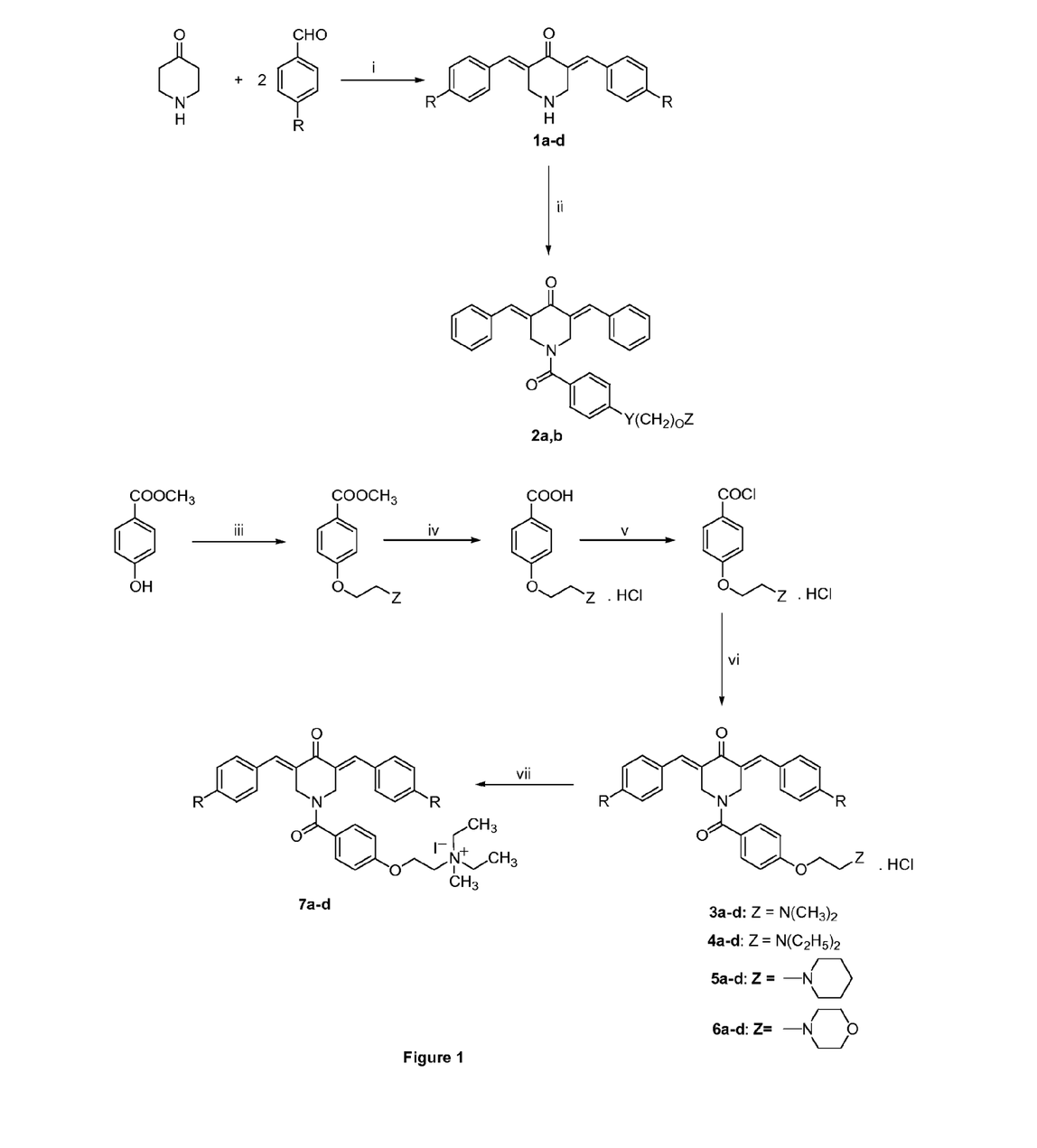
FIG. 1 is a schematic representation of the synthesis of some of the compounds of the invention.

The synthetic chemical routes employed in producing the compounds of series 1-7 are portrayed in FIG. 1. The compounds in series 1 were prepared by acid-catalyzed condensation between various aryl aldehydes and 4-piperidone. The reaction of 1a with different aroyl chlorides led to the isolation of 2a,b. Alkylation of methyl 4-hydroxybenzoate with 2-dimethylaminoethyl hydrochloride gave rise to the corresponding ether which upon hydrolysis produced 4-(2-dimethylaminoethyloxy)benzoic acid isolated as the hydrochloride salt. This compound was converted to the corresponding acid chloride which condensed with 1a-d leading to the formation of 3a-d, respectively. A similar synthetic pathway was employed using related N-(2-chloroethyl)amines hydrochlorides in place of 2-dimethylaminoethyl hydrochloride leading to the formation of 4a-d, 5a-d and 6a-d. Reaction of the free bases derived from 4a-d with methyl iodide gave rise to the corresponding quaternary ammonium salts 7a-d. In addition, the preparation of 4-(2-diethylaminoethoxy)benzoic acid 10, which is structurally related to the compounds in series 4, was synthesized.

In FIG. 1, the substituents R in series 1, 3-7 are as follows: a=R=H; b: R=Cl; c: R=$NO_2$; d: R=$CH_3$. The nature of the $Y(CH_2)_oZ$ moieties in series 2 are a: $Y(CH_2)_oZ$=H; b: $Y(CH_2)_oZ$=$OCH_3$. The following reagents were used in the synthetic routes viz i=HCl/$CH_3COOH$; ii=ClCO$C_6H_4Y(CH_2)_oZ$; iii=$ClCH_2CH_2$ZHCl/$K_2CO_3$; iv=NaOH/HCl; v=$SOCl_2$; vi=1a-d; vii=$CH_3$I/$K_2CO_3$.

Melting points are uncorrected. Elemental analyses (C, H, N) were undertaken on 1d and 2-7 by the Microanalytical Laboratory, Department of Chemistry, University of Alberta and were within 0.4% of the calculated values. Compounds 3b-d, 4a, 5a,d, 6a,c,d and 7a,d were isolated as the hemihydrates, 7b as the monohydrate and 5c was obtained with 1.5 moles of water of crystallization. The $^1$H NMR spectra (500 MHz) of all of the compounds in series 1-10 and the $^{13}$C NMR spectra (125 MHz) of representative compounds were determined in deuterated solvents using a Bruker AM 500 FT NMR machine.

Synthesis of 1a-d: Compounds 1a-d were prepared by a literature procedure (Journal of Medicinal Chemistry 44, 586 (2001). Generally, the appropriate aryl aldehyde (36.71 mmol) was added to a suspension of 4-piperidone hydrochloride monohydrate (13.03 mmol) in acetic acid (35 mL). Dry hydrogen chloride was passed through this mixture for 0.5 hours during which time a clear solution was obtained. After stirring at room temperature for 24 hours, the precipitate was collected and added to a mixture of a saturated aqueous potassium carbonate solution (25% w/v, 25 mL) in acetone (25 mL); the resultant mixture was stirred for 0.5 hours. The free base was collected, washed with water (50 mL) and dried. The compounds were recrystallized. 1d was recrystallized from chloroform-ethanol to give the desired product.

3,5-bis(4-Methylphenylmethylene)-4-piperidone (1d). M.p. 180-181° C. Yield: 79%. $^1$H NMR (CDCl$_3$): 2.40 (s, 6H), 4.16 (s, 4H), 7.24 (d, 2H, J=7.75 Hz), 7.31 (d, 2H, J=7.85 Hz), 7.80 (s, 2H). Found C, 82.87; H, 6.94; N, 4.60%. Anal. ($C_{26}H_{21}NO_2$) requires C, 83.13; H, 6.98; N, 4.62%.

General procedure for the synthesis of 2a, b: A solution of the aroyl chloride (0.015 mol) in 1,2-dichloroethane (50 ml) was added over 0.5 h to a solution of 1a (0.01 mol) and triethylamine (0.03 mol) in 1,2-dichloroethane (30 ml) at ~5-6° C. After stirring at room temperature for 6 h, the solvent was removed in vacuo. An aqueous solution of potassium carbonate (10% w/v, 50 ml) was added to the residue and the resultant slurry was stirred for 4 h at room temperature. The precipitate was collected, washed with water and dried. The products were purified by crystallization from chloroform-methanol.

1-Benzoyl-3,5-bis(phenylmethylene)-4-piperidone (2a). M.p. 165-166°. Yield: 85%. $^1$H NMR (CDCl$_3$): 4.72 (bs, 2H), 5.04 (bs, 2H), 7.06 (t, 2H), 7.22 (d, 4H), 7.38 (bs, 9H), 7.92 (s, 2H). Found C, 82.02; H, 5.49; N, 3.56%. Anal. ($C_{26}H_{21}NO_2$) requires C, 82.30; H, 5.58; N, 3.69%.

1-(4-Methoxybenzoyl)-3,5-bis(phenylmethylene)-4-piperidone (2b). M.p. 177-178°. Yield: 72%. $^1$H NMR (CDCl$_3$): 3.70 (s, 3H), 4.87 (bs, 4H), 6.51 (d, 2H, J=10.62 Hz), 7.17 (d, 2H, J=10.69 Hz), 7.40 (bs, 10H), 10.07 (s, 2H). Found C, 79.19; H, 5.72; N, 3.25%. Anal. ($C_{27}H_{23}NO_3$) requires C, 79.19; H, 5.66; N, 3.42%.

General procedure for the synthesis of series 3-6: The general method employed for the preparation of the compounds in series 3-6 is exemplified by the synthesis of 4a. A mixture of 10 vide infra (4.10 g, 0.015 mole), thionyl chloride (23.10 g, 2 mol) and dimethylformamide (0.01 ml) was heated under reflux for 3 h. Evaporation in vacuo led to the isolation of the corresponding acid chloride which was dissolved in 1,2-dichloroethane (50 ml) and added over a period of 0.5 h to a solution of 1a (2.75 g, 0.01 mol) and triethylamine (3.03 g, 0.03 mol) in 1,2-dichloroethane (30 ml) at ~5-6° C. After stirring at room temperature for 6 h, the solvent was removed in vacuo. The solid obtained was suspended in a solution of potassium carbonate (10% w/v, 50 ml) and stirred at room temperature for 4 h. The precipitate was collected, washed with water and dried to give 1-[4-(2-diethylaminoethyloxy)phenylcarbonyl]-3,5-bis(phenylmethylene)-4-piperidone, i.e., the free base corresponding to 4a. The hydrochloride salt was prepared by dissolving the free base in a mixture of isopropanol and chloroform (3:2; 50 ml) and after the addition of activated charcoal (0.5 g), the mixture was stirred at room temperature for 1 h. The solution was acidified with dry hydrogen chloride gas and the mixture stirred at room temperature for 1 h. The solvent was removed in vacuo to yield a viscous oil to which was added acetone (50 ml) and the mixture was heated under reflux for 0.5 h. On cooling to room temperature, the precipitate was collected and recrystallized from acetone to give 4a. The analogs 4b-d were prepared using the same methodology except isopropanol was used as the recrystallization solvent for 4b and 4c. Series 3, 5 and 6 were obtained in a similar manner from methyl 4-hydroxybenzoate and the appropriate 2-chloro-N-substituted-ethylamine hydrochloride. The solvent used in recrystallizing 3a-d, 5a,b and 6a-d was isopropanol. Diethyl ether-methanol was used to purify 5c, while 5d was recrystallized from acetone.

[4-(2-Dimethylaminoethoxy)phenylcarbonyl]-3,5-bis(phenylmethylene)-4-piperidone hydrochloride (3a). M.p. 244-245°. Yield: 76%. $^1$H NMR (DMSO-d$_6$): 2.83 (s, 6H), 3.46 (t, 2H), 4.22 (t, 2H), 4.80 (bs, 4H), 6.55 (d, 2H, J=10.55 Hz), 7.08 (d, 2H, J=10.65 Hz), 7.37 (bs, 10H), 7.76 (s, 2H), 11.08 (bs, 1H). Found C, 71.80; H, 5.90; N, 5.50%. Anal. (C$_{30}$H$_{31}$ClN$_2$O$_3$) requires C, 71.63; H, 6.21; N, 5.57%.

3,5-bis(4-Chlorophenylmethylene)-1-[4-(2-dimethylaminoethoxy)phenyl-carbonyl]-4-piperidone hydrochloride hemihydrate (3b). M.p. 250-251°. Yield: 71%. $^1$H NMR (DMSO-d$_6$): 2.92 (s, 6H), 3.47 (t, 2H), 4.22 (t, 2H), 4.81 (bs, 4H), 6.58 (d, 2H, J=7.61 Hz), 7.14 (d, 2H, J=7.65 Hz), 7.39 (m, 8H), 7.82 (d, 2H, J=10.75 Hz), 12.84 (bs, 1H). Found C, 62.45; H, 5.15; N, 4.86%. Anal. (C$_{30}$H$_{29}$Cl$_3$N$_2$O$_3$.0.5H$_2$O) requires C, 62.02; H, 5.03; N, 4.82%.

1-[4-(2-Dimethylaminoethoxy)phenylcarbonyl]-3,5-bis(4-nitrophenylmethylene)-4-piperidone hydrochloride hemihydrate (3c). M.p. 215-217°. Yield: 62%. $^1$H NMR (DMSO-d$_6$): 2.78 (s, 6H), 3.42 (t, 2H), 4.21 (t, 2H), 4.85 (bs, 4H), 6.70 (d, 2H, J=10.28 Hz), 7.15 (d, 2H, J=10.25 Hz), 7.72 (m, 4H), 7.82 (s, 2H), 10.27 (bs, 4H), 11.08 (bs, 1H). Found C, 59.45; H, 4.93; N, 9.08%. Anal. (C$_{30}$H$_{29}$ClN$_4$O$_7$.0.5H$_2$O) requires C, 59.85; H, 4.85; N, 9.30%.

1-[4-(2-Dimethylaminoethoxy)phenylcarbonyl]-3,5-bis(4-methylphenyl-methylene)-4-piperidone hydrochloride hemihydrate (3d). M.p. 224-226°. Yield: 64%. $^1$H NMR (CDCl$_3$): 2.40 (s, 6H), 2.90 (t, 2H), 3.43 (t, 2H), 4.42 (t, 2H), 4.87 (bs, 4H), 6.58 (d, 2H, J=10.10 Hz), 7.23 (m, 10H), 7.88 (s, 2H), 13.08 (br s, 1H). Found C, 71.38; H, 6.75; N, 5.21%. Anal. (C$_{32}$H$_{35}$ClN$_2$O$_3$.0.5H$_2$O) requires C, 71.16; H, 6.53; N, 5.18%.

1-[4-(2-Diethylaminoethoxy)phenylcarbonyl]-3,5-bis(phenylmethylene)-4-piperidone hydrochloride hemihydrate (4a). M.p. 184-185°. Yield: 72%. $^1$H NMR (CDCl$_3$): 1.45 (t, 6H, 2×CH$_3$), 3.22 (m, 4H, 2×NCH$_2$CH$_3$), 3.40 (t, 2H, OCH$_2$CH$_2$N), 4.41 (t, 2H, OCH$_2$CH$_2$N), 4.85 (bs, 4H, 2× piperidyl NCH$_2$), 6.50 (d, 2H, aryl H, J=10.1 Hz), 7.17 (d, 2H, aryl H, J=9.05 Hz), 7.44 (bs, 10H, aryl H), 7.92 (s, 2H, =CH), 12.70 (s, 1H, NH). $^{13}$C NMR (CDCl$_3$): 187.41 (CO), 170.14 (—CO—N—), 158.77, 134.88, 132.21, 130.77, 130.08, 129.70, 129.25, 127.99, 114.19, 63.05 (OCH$_2$), 50.95 (OCH$_2$—CH$_2$—N), 47.39 (NCH$_2$), 10.89 (CH$_3$). Found C, 71.22; H, 6.41; N, 4.79%. Anal. (C$_{32}$H$_{35}$ClN$_2$O$_3$.0.5H$_2$O) requires C, 71.16; H, 6.71; N, 5.18%.

3,5-bis(4-Chlorophenylmethylene)-1-[4-(2-diethylaminoethoxy)phenylcarbonyl]-4-piperidone hydrochloride (4b). M.p. 210-211°. Yield: 68%. $^1$H NMR (CDCl$_3$): 1.45 (t, 6H), 3.22 (bs, 4H), 3.41 (t, 2H), 4.45 (t, 2H), 4.81 (bs, 4H), 6.57 (d, 2H, J=10.34 Hz), 7.17 (d, 2H, J=10.30 Hz), 7.31 (m, 4H), 7.41 (d, 2H, J=6.54 Hz), 7.84 (s, 2H), 12.70 (bs, 1H). Found C, 64.28; H, 5.26; N, 4.98%. Anal. (C$_{32}$H$_{33}$Cl$_3$N$_2$O$_3$) requires C, 64.06; H, 5.54; N, 4.67%.

1-[4-(2-Diethylaminoethoxy)phenylcarbonyl]-3,5-bis(4-nitrophenylmethylene)-4-piperidone hydrochloride (4c). M.p. 197-198°. Yield: 61%. $^1$H NMR (CDCl$_3$): 1.46 (t, 6H), 3.19 (bs, 2H), 3.26 (bs, 2H), 4.45 (t, 2H), 4.45 (t, 2H), 4.82 (bs, 4H), 6.60 (d, 2H, J=10.25 Hz), 7.14 (d, 2H, J=10.25 Hz), 7.51 (bs, 4H), 7.89 (s, 2H), 10.26 (d, 2H, J=6.35 Hz), 12.57 (bs, 1H). Found C, 62.06; H, 5.38; N, 9.19%. Anal. (C$_{32}$H$_{33}$ClN$_4$O$_7$) requires C, 61.88; H, 5.36; N, 9.02%.

1-[4-(2-Diethylaminoethoxy)phenylcarbonyl]-3,5-bis(4-methylphenylmethylene)-4-piperidone hydrochloride (4d). M.p. 204-205°. Yield: 62%. $^1$H NMR (CDCl$_3$): 1.45 (t, 6H), 2.40 (s, 6H), 3.22 (m, 4H), 3.40 (t, 2H), 4.46 (t, 2H), 4.87 (bs, 4H), 6.57 (d, 2H, J=10.53 Hz), 7.23 (d, 2H, J=10.37 Hz), 7.32 (m, 4H), 7.88 (s, 2H), 12.62 (bs, 1H). Found C, 73.34; H, 6.86; N, 5.36%. Anal. (C$_{34}$H$_{39}$ClN$_2$O$_3$) requires C, 73.04; H, 7.03; N, 5.01%.

1-[4-{2-(1-Piperidinyl)ethoxy}phenylcarbonyl]-3,5-bis(phenylmethylene)-4-piperidone hydrochloride hemihydrate (5a). M.p. 214-215°. Yield: 52%. $^1$H NMR (CDCl$_3$): 1.43 (t, 1H), 1.88 (t, 3H), 2.28 (q, 2H), 2.76 (t, 2H), 3.34 (bs, 2H), 3.60 (t, 2H), 4.44 (bs, 2H), 4.86 (bs, 4H), 6.50 (d, 2H, J=7.75 Hz), 7.16 (d, 2H, J=7.2 Hz), 7.38 (bs, 10H), 7.90 (s, 2H), 12.61 (bs, 1H). Found C, 71.48; H, 6.38; N, 5.04%. Anal. (C$_{33}$H$_{35}$ClN$_2$O$_3$.0.5H$_2$O) requires C, 71.79; H, 6.38; N, 5.07%.

3,5-bis(4-Chlorophenylmethylene)-1-[4-{2-(1-piperidinyl)ethoxy}phenylcarbonyl]-4-piperidone hydrochloride (5b). M.p. 257-258°. Yield: 75%. $^1$H NMR (CDCl$_3$): 1.44 (q, 1H), 1.92 (t, 3H), 2.32 (q, 2H), 2.80 (q, 2H), 3.38 (bs, 2H), 3.63 (d, 2H, J=10.23 Hz), 4.54 (bs, 2H), 4.80 (bs, 4H), 6.57 (d, 2H, J=7.84 Hz), 7.17 (d, 2H, J=7.99 Hz), 7.34 (m, 8H), 7.90 (s, 2H), 12.68 (bs, 1H). Found C, 64.35; H, 5.39; N, 4.45%. Anal. (C$_{33}$H$_{33}$Cl$_3$N$_2$O$_3$) requires C, 64.77; H, 5.44; N, 4.58%.

3,5-bis(4-Nitrophenylmethylene)-1-[4-{2-(1-piperidinyl)ethoxy}phenylcarbonyl]-4-piperidone hydrochloride 1.5 hydrate (5c). M.p. 224-226°. Yield: 64%. $^1$H NMR (DMSO-d$_6$): 1.42 (t, 1H), 1.81 (t, 3H), 2.04 (q, 2H), 2.86 (q, 2H), 3.36 (d, 2H), 3.48 (m, 2H), 4.32 (bs, 2H), 4.75 (bs, 4H), 6.56 (d, 2H, J=10.25 Hz), 7.07 (d, 2H, J=10.10 Hz), 7.60 (m, 4H), 7.78 (s, 2H), 10.16 (bs, 4H), 11.53 (s, 1H). Found C, 71.38; H, 6.75; N, 5.21%. Anal. (C$_{32}$H$_{35}$ClN$_2$O$_3$.1.5H$_2$O) requires C, 71.16; H, 6.53; N, 5.18%.

3,5-bis(4-Methyl phenylmethylene)-1-[4-{1-piperidinyl)ethoxy}phenylcarbonyl]-4-piperidone hydrochloride hemihydrate (5d). M.p. 105° (dec). Yield: 65%. $^1$H NMR (CDCl$_3$): 1.42 (q, 1H), 1.89 (t, 3H), 2.22 (q, 2H), 2.80 (bs, 2H), 3.40 (bs, 2H), 3.65 (d, 2H, J=9.56 Hz), 4.48 (bs, 2H), 4.88 (bs, 4H), 5.44 (bs, 2H), 6.56 (d, 2H, J=7.91 Hz), 7.23 (m, 10H), 7.99 (s, 2H), 11.80 (bs, 1H). Found C, 71.38; H, 6.75; N, 5.21%. Anal. (C$_{32}$H$_{35}$ClN$_2$O$_3$.0.5H$_2$O) requires C, 71.16; H, 6.53; N, 5.18%.

1-[4-{2-(4-Morpholinyl)ethoxy}phenylcarbonyl]-3,5-bis(phenylmethylene)-4-piperidone hydrochloride hemihydrate (6a). M.p. 208-209°. Yield: 73%. $^1$H NMR (CDCl$_3$): 3.05 (q, 2H), 3.40 (bs, 2H), 3.53 (d, 2H, J=12.02 Hz), 4.02 (dd, 2H), 4.30 (t, 2H), 4.47 (bs, 2H), 4.86 (bs, 4H), 6.51 (d, 2H, J=10.56 Hz), 7.19 (d, 2H, J=10.50 Hz), 7.44 (bs, 10H), 7.92 (s, 2H), 13.69 (bs, 1H). Found C, 69.54; H, 5.95; N, 4.96%. Anal. (C$_{32}$H$_{33}$ClN$_2$O$_4$.0.5H$_2$O) requires C, 69.36; H, 6.00; N, 5.05%.

3,5-bis(4-Chlorophenylmethylene)-1-[4-{2-(4-morpholinyl)ethoxy}phenylcarbonyl-4-piperidone hydrochloride (6b). M.p. 240-241°. Yield: 74%. $^1$H NMR (CDCl$_3$): 3.06 (bs, 2H), 3.40 (bs, 2H), 3.55 (d, 2H, J=11.97 Hz), 4.29 (t, 2H), 4.30 (t, 2H), 4.50 (t, 2H), 4.81 (bs, 4H), 6.59 (d, 2H, J=7.30 Hz), 7.14 (d, 2H, J=7.47 Hz), 7.51 (m, 4H), 7.90

(s, 2H), 10.26 (bs, 4H), 13.59 (s, 1H). Found C, 62.39; H, 4.94; N, 4.47%. Anal. ($C_{32}H_{31}Cl_3N_2O_4$) requires C, 62.60; H, 5.09; N, 4.56%.

1-[4-{2-(4-Morpholinyl)ethoxy}phenylcarbonyl]-3,5-bis (4-nitrophenylmethylene)-4-piperidone hydrochloride hemihydrate (6c). M.p. 224-226°. Yield: 64%. $^1$H NMR (CDCl$_3$): 3.05 (q, 2H), 3.40 (bs, 2H), 3.53 (d, 2H, J=12.02 Hz), 4.02 (dd, 2H), 4.30 (t, 2H), 4.47 (bs, 2H), 4.86 (bs, 4H), 6.51 (d, 2H, J=10.56 Hz), 7.19 (d, 2H, J=10.50 Hz), 7.44 (bs, 10H), 7.92 (s, 2H), 13.59 (bs, 1H). Found C, 59.52; H, 4.72; N, 10.51%. Anal. ($C_{32}H_{31}ClN_4O_8.0.5H_2O$) requires C, 59.67; H, 4.85; N, 10.69%.

3,5-bis(4-Methyl phenylmethylene)-1-[4-{2-(4-morpholinyl)ethoxy}phenylcarbonyl]-4-piperidone hydrochloride hemihydrate (6d). M.p. 235-236°. Yield: 66%. $^1$H NMR (CDCl$_3$): 2.40 (s, 3H), 3.03 (m, 2H), 3.40 (bs, 2H), 3.54 (d, 2H, J=11.98 Hz), 4.02 (dd, 2H), 4.29 (t, 2H), 4.50 (bs, 2H), 4.87 (s, 4H), 6.58 (d, 2H, J=10.63 Hz), 7.24 (m, 10H), 7.88 (s, 2H), 13.68 (bs, 1H). Found C, 70.39; H, 6.69; N, 4.79%. Anal. ($C_{34}H_{37}ClN_2O_4.0.5H_2O$) requires C, 70.15; H, 6.57; N, 4.81%.

General procedure for the synthesis of 7a-d: Activated charcoal (0.5 g) was added to a solution of the free base of 4a vide supra (4.95 g, 0.01 mol) in acetone (25 ml) and the mixture was stirred at room temperature for 1 h. The suspension was filtered via celite and the celite bed was washed with acetone (10 ml). Methyl iodide (2.13 g, 0.015 mol) was added to the combined filtrates and the mixture was stirred at room temperature for 4-5 h. The resultant precipitate was collected, dried and recrystallized from diethyl ether/methanol to give the desired products.

1-[4-(2-Diethylaminoethoxy)phenylcarbonyl]-3,5-bis (phenylmethylene)-4-piperidone methoiodide (7a). M.p. 161-162°. Yield: 85%. $^1$H NMR (CDCl$_3$): 1.45 (t, 6H, 2×CH$_3$), 3.34 (s, 3H, N—CH$_3$), 3.70 (m, 4H, 2×NC$\underline{H}_2$CH$_3$), 4.17 (bs, 2H, OC$\underline{H}_2$CH$_2$N), 4.39 (bs, 2H, OCH$_2$C$\underline{H}_2$N), 4.86 (bs, 4H, piperidyl H), 6.56 (d, 2H, aryl H, J=10.58 Hz), 7.19 (d, 2H, aryl H, J=10.03 Hz), 7.39 (bs, 12H, aryl H), 7.91 (s, 2H, olefinic H). Found C, 61.11; H, 5.64; N, 4.23%. Anal. ($C_{33}H_{37}IN_2O_3.0.5H_2O$) requires C, 61.39; H, 5.77; N, 4.33%.

3,5-bis(4-Chlorophenylmethylene)-1-[4-(2-diethylaminoethoxy)phenylcarbonyl]-4-piperidone methoiodide (7b). M.p. 220-223°. Yield: 69%. $^1$H NMR (DMSO-d$_6$): 1.32 (t, 6H), 3.07 (d, 3H, J=7.99 Hz), 3.45 (t, 4H), 3.74 (t, 2H), 4.30 (bs, 1H), 4.39 (bs, 1H), 4.61 (bs, 4H), 6.60 (d, 1H, J=10.22 Hz), 7.11 (d, 1H, J=10.35 Hz), 7.23 (d, 1H, J=10.36 Hz), 7.71 (bs, 1H), 7.89 (s, 2H). Found C, 54.44; H, 4.79; N, 3.75%. Anal. ($C_{33}H_{35}Cl_2IN_2O_3.0.5H_2O$) requires C, 54.78; H, 4.87; N, 3.92%.

1-[4-(2-Diethylaminoethoxy)phenylcarbonyl]-3,5-bis(4-nitrophenylmethylene)-4-piperidone methoiodide (7c). M.p. 193-195° (dec). Yield: 74%. $^1$H NMR (DMSO-d$_6$): 1.24 (t, 6H), 3.00 (s, 3H), 3.38 (q, 4H), 3.64 (t, 2H), 4.27 (t, 2H), 4.40 (bs, 4H), 6.70 (d, 2H, J=10.41 Hz), 7.16 (d, 2H, J=10.39 Hz), 7.74 (bs, 4H), 7.83 (s, 2H), 10.27 (bs, 4H). Found C, 54.41; H, 4.71; N, 7.60%. Anal. ($C_{33}H_{35}IN_4O_7$) requires C, 54.55; H, 4.86; N, 7.71%.

1-[4-(2-Diethylaminoethoxy)phenylcarbonyl]-3,5-bis(4-methylphenylmethylene)-4-piperidone methoiodide (7d). M.p. 212-213°. Yield: 72%. $^1$H NMR (DMSO-d$_6$): 1.24 (t, 6H), 2.34 (s, 6H), 3.01 (s, 3H), 3.39 (q, 4H), 3.68 (t, 2H), 4.33 (t, 4H), 4.87 (bs, 4H), 6.75 (d, 2H, J=10.34 Hz), 7.22 (d, 2H, J=10.30 Hz), 7.28 (m, 8H), 7.72 (s, 2H). Found C, 62.65; H, 6.25; N, 4.10%. Anal. ($C_{35}H_{41}IN_2O_3.0.5H_2O$) requires C, 62.40; H, 6.13; N, 4.15%.

Synthesis of 8a: 3,5-bis(thiophen-2-ylmethylene)-piperidin-4-one hydrochloride (8a): 8a was prepared in the same manner as 1d. The reaction of 4-piperidone hydrochloride with 2-thiophene-carboxaldehyde afforded 8a, m.p. 297(dec) in 72% yield. δ (DMSO-d$_6$): 4.45 (brs, 4H, 2×NCH$_2$), 7.32 (t, 2H, 2×C$_3$—H), 7.70 (s, 2H, 2×=CH-ylidene protons), 7.94-8.05 (d, 4H, 2×C$_2$—H & 2×C$_4$—H). Found C, 55.36%; H, 4.30%; N, 4.19%. $C_{15}H_{14}ClNOS_2$ requires C, 55.63%; H, 4.36%; N, 4.32%.

Synthesis of 9a: 1-[4-(2-Diethylamino-ethoxy)phenylcarbonyl]-3,5-bis(thiophene-2-ylmethylen)-piperidin-4-one hydrochloride monohydrate (9a): Following the above procedure described for compound 4a, the reaction of 3,5-bis (thiophen-2-ylmethylene)-piperidin-4-one with V. HCl (X=CO, T=OH, Y=O, o=2, Z=N(C$_2$H$_5$)$_2$) (0.015 mol) afforded 9a, m.p. 193-194° in 82% yield. δ (CDCl$_3$): 1.44-1.47 (t, 6H, 2×CH$_3$), 3.17-3.31 (m, 4H, 2×NCH$_2$), 3.56 (br s, 2H, NCH$_2$), 4.53 (t, 2H, OCH2), 4.93 (br s, 4H, 2×NCH$_2$), 6.75-6.77 (d, 2H, C$_2$—H & C$_6$—H), 7.18-7.19 (t, 2H, 2×C$_3$'—H), 7.38-7.40 (d, 4H, C$_3$—H, C$_5$—H & 2×C$_4$'—H), 7.66-7.67 (d, 2H, C$_2$'—H), 12.67 (s, 1H, NH). Found C, 59.90%; H, 5.76%; N, 4.81%. $C_{28}H_{31}ClN_2O_3S_2.H_2O$ requires C, 59.92%; H, 5.56%; N, 4.99%.

Synthesis of 10: A mixture of methyl 4-hydroxybenzoate (15.21 g, 0.1 mol), anhydrous potassium carbonate (34.55 g, 0.25 mol), 2-chloro-N,N-diethylamine hydrochloride (25.81 g, 0.15 mol), potassium iodide (0.166 g, g, 0.001 mol) and acetone (75 ml) was heated under reflux for 10-9 h. On cooling, the solid was removed by filtration and the solvent was evaporated. The residue was dissolved in toluene (75 ml) and the solution was washed with sodium hydroxide solution (2% w/v, 30 ml) and deionized water (2×30 ml). Removal of the solvent afforded methyl 4-(2-diethylaminoethyloxy)benzoate as an oil which was dissolved in ethanol (50 ml) and added to a solution of sodium hydroxide (10.0 g, 0.2 mol) in water (50 ml). The mixture was heated under reflux for 2 h. The ethanol was removed in vacuo and the aqueous solution was acidified with hydrochloric acid (12N) at 5-6° C. The solid was collected, triturated with water (previously cooled to 5-6° C.), filtered and dried at 55-60° C. in vacuo and recrystallized from water to give 10. 4-(2-Diethylaminoethoxy)benzoic acid hydrochloride (10). M.p. 170-172° [lit. [22], m.p. 171-174°]. Yield: 73%. $^1$H NMR (D$_2$O): 1.17-1.20 (t, 6H, 2×CH$_3$), 3.13-3.24 (m, 4H, 2×CH$_2$), 3.47-3.48 (t, 2H, OCH$_2$C$\underline{H}_2$N), 4.26-4.28 (t, 2H, OC$\underline{H}_2$CH$_2$N), 6.89-6.91 (d, 2H, aryl H), 7.80-7.82 (d, 2H, aryl H).

Biological Activity

Cytotoxic evaluations against Molt 4/C8, CEM and L1210 cells: All of the compounds in series 1-7 were evaluated against human Molt 4/C8 and CEM T-lymphocytes as well as murine L1210 cells. In addition, compound 10 was included in these assays. These data are presented in Table 1. The cytotoxic potencies of various compounds towards a panel of various human tumour cell lines are given in Table 2.

The compounds in series 1-7 and 10 and melphalan were evaluated against Molt 4/C8, CEM and L1210 cells by a literature procedure (J. Balzarini, E. De Clercq, M. P. Mertes, D. Shugar, P. F. Torrence, Biochem. Pharmacol. 31 (1982) 3673-3682). In these assays, at least three different concentrations of compounds were incubated with the neoplastic cells at 37° for 48 h after which time inhibition of growth was determined.

Selected 4-piperidones were examined for antineoplastic properties towards a panel of 49 (38-59) human tumour cell lines using a literature method (M. R. Boyd, K. D. Paull, Drug. Dev. Res. 34 (1995) 91-109). In addition, both 5-fluorouracil and melphalan were evaluated towards 57 cell lines. In this assay, compounds were incubated for 48 h using five different concentrations at series tenfold dilutions of $10^{-10.3}$M to $10^{-4.3}$M except for 1a, 4a ($10^{-8}$M to $10^{-4}$), 5-fluorouracil ($10^{-6.6}$M to $10^{-2.6}$M) and melphalan ($10^{-7.6}$M to $10^{-3.6}$M). The mean graph midpoint (MG MID) figures for 1a, 3b, 3d, 5d, 7d and melphalan were $IC_{50}$ values. MG MID is the average of the potencies of the compound to approximately 50 neoplastic cell lines. In the following cases, the number of cell lines compared to the total number of cell lines for which an $IC_{50}$ figure were not obtained were as follows [maximum or minimum concentrations (molar) in parentheses], namely 4a: 2/53 ($<10^{-10}$), 5b: 2/50 ($>10^{4.3}$), 6a: 3/48 ($>10^{-4.3}$)), 6b: 11/38 ($<10^{-10.3}$), 6d: 3/44 ($<10^{-10.3}$), 7a: 36/52 ($>10^{-4.3}$) and 5-fluorouracil 3/57 ($>10^{-2.6}$).

Rankings of potencies of the compounds in series 3-7: The first investigation involved comparing the $IC_{50}$ values of those compounds in series 3-7 which had the same substituents in the arylidene aryl ring. The scores for the compounds in each of the Molt 4/C8, CEM and L1210 cell lines were obtained as follows. The compound having the highest potency was assigned a value of 5, the compound with the next lowest $IC_{50}$ figures was given a rating of 4 and so forth; the amide with lowest potency was given a figure of 1. The standard deviations for each $IC_{50}$ value were taken into consideration. The scores available for equipotent compounds were divided equally and a total of 15 points were awarded for each of the comparisons. The second analysis was designed to find the optimal substitution pattern in the arylidene aryl rings in the three cell lines. Thus in each of the series 3-7, the most potent compound was given a rating of 4, the second most potent analog 3 and so forth. A total of ten points were used in each comparison. Standard deviations were taken into consideration and the scores for compounds having the same potencies were divided equally.

Determination of MDR-reversal properties: The methodology used in evaluating the capacity of the compounds to reverse multiple drug resistance (MDR) has been described previously (Kawase, M.; Sakagami, H.; Motohashi, N.; Hauer, H.; Chatterjee, S. S.; Spengler, G.; Vigyikanne, A. V.; Molnár, A.; Molnár, J. In Vivo 2005, 19, 705-712). In brief, both the L-5178 MDR and parental cells were grown in McCoy's 5A medium containing heat-inactivated horse serum (10%), L-glutamine and antibiotics. A solution of the test compound (2 mg/ml, 10 µl) in dimethylsulfoxide was added to aliquots of the cell suspension and incubated at room temperature for 10 minutes. Then 10 µl of rhodamine 123 in dimethylsulfoxide was added so that its final concentration was 5.2 µM and the cells were incubated for a further 20 minutes at 37° C. The cells were washed twice and resuspended in PBS (pH 7.4) after which the fluorescence was measured using a Beckton Dickinson FACScan instrument. The fluorescence of the cells was measured in treated MDR cells (F1), untreated MDR cells (F2), treated parental cells (F3) and the FAR values were obtained from the following equation, viz (F1/F2)/(F3/F4).

Cytotoxicity evaluations towards various cell lines: The $CC_{50}$ (cytotoxicity dose) values of the compounds in series 1 and 3 to 7 towards HSC-2, HSC-4, HGF, HPC, HL-60 and HPLF cells were determined using a literature method involving the MTT assay (Kawase, M.; Sakagami, H.; Motohashi, N.; Hauer, H.; Chatterjee, S. S.; Spengler, G.; Vigyikanne, A. V.; Molnár, A.; Molnár, J. In Vivo 2005, 19, 705-712; and Takeuchi, R.; Hoshijima, H.; Onuki, N.; Nagasaka, H.; Chowdhury, S. A.; Kawase, M.; Sakagami, H. Anticancer Res. 2005, 25, 4037-4042) (MTT assay is a laboratory test for measuring cellular proliferation (cell growth). MTT stands for 3-(4,5-dimethylthiazol-2-yl)-2,5-diphenyltetrazolium bromide). The cells were incubated with varying concentrations of the compounds along with untreated cells for 24 h and the absorbance at 540 nm measured. In the case of the HL-60 assay, the trypan blue exclusion method was followed and cell viability was determined using a haemocytometer. The $CC_{50}$ values were obtained from dose-response curves (Sakagami, H.; Satoh, K.; Ohata, H.; Takahashi, H.; Yoshida, H.; Iida, M.; Kuribayashi, N.; Sakagami, T.; Momose, K.; Takeda, M. Anticancer Res. 1996, 16, 2635-2644). The general methods used in culturing the cells employed in these cytotoxicity experiments have been described previously (Kawase, M.; Sakagami, H.; Motohashi, N.; Hauer, H.; Chatterjee, S. S.; Spengler, G.; Vigyikanne, A. V.; Molnár, A.; Molnár, J. In Vivo 2005, 19, 705-712; and Takeuchi, R.; Hoshijima, H.; Onuki, N.; Nagasaka, H.; Chowdhury, S. A.; Kawase, M.; Sakagami, H. Anticancer Res. 2005, 25, 4037-4042). In brief, the malignant cells were obtained from Professor Nagumo, Showa University, Japan. The HGF, HPC and HPLF cells were prepared from human periodontal tissue after obtaining informed consent according to the guidelines of Meikai University Ethics Committee, Japan (No. 0206). Since normal cells have a short lifespan, cells at the 3-7 population doubling time were used. With the exception of the HL-60 neoplasm, the cells were cultured in DMEM containing heat-inactivated FBS (10%) at 37° C. in a humidified carbon dioxide atmosphere and subcultured by trypsinization. The HL-60 cells were cultured in a similar fashion except that RPMI 1640 media was employed.

All references mentioned herein are incorporated by reference.

TABLE 1

Potencies of the compounds in series 1-7 and 10 towards human Molt 4/C8 and CEM T-lymphocytes and murine L1210 cells[a]

| Compound ID | $IC_{50}$ (µM) | | | | | |
|---|---|---|---|---|---|---|
| | Molt 4/C8 Cells | SD | CEM cells | SD | L1210 cells | SD |
| 1a | | 0.15 | | 0.02 | | 0.11 |
| 1b | | 4.0 | | 0.48 | | 0.3 |
| 1c | | 0.75 | | 2.28 | | 4.2 |
| 1d | | 0.09 | | 0 | | 0.14 |
| 2a | | 0.07 | | 0.03 | | 0 |
| 2b | | 0.73 | | 3.33 | | 3.7 |
| 3a | 0.58 | 0.09 | | 0.57 | | 0.10 |
| 3b | | 0.57 | | 0.67 | | 1.30 |
| 3c | 0.314 | 0.035 | 0.319 | 0.013 | | 0.71 |
| 3d | | 0.21 | 0.884 | 0.532 | | 133 |
| 4a | | 0.15 | | 0.15 | | 0.43 |
| 4b | | 14.9 | | 5.9 | | 4.7 |
| 4c | 0.31 | 0.01 | 0.34 | 0.01 | | 0.20 |
| 4d | | 0.45 | | 0.30 | | 0.08 |
| 5a | | 0.12 | | 0.64 | | 0.22 |
| 5b | | 19.5 | | 2.99 | | 47 |
| 5c | 0.33 | 0.011 | 0.315 | 0.002 | | 2.47 |
| 5d | 0.91 | 0.45 | | 0.73 | | 1.64 |
| 6a | | 0.16 | | 0.09 | | 13 |
| 6b | | 10.1 | | 1.00 | | 54.6 |
| 6c | 0.343 | 0.013 | 0.379 | 0.032 | | 1.08 |
| 6d | | 0.21 | | 0.13 | | 9.6 |
| 7a | | 82 | | 12 | | 30 |
| 7b | | 20.6 | | 43.6 | | 230 |
| 7c | | 2.9 | | 5.2 | | 0.9 |
| 7d | | 2.6 | | 4.3 | | 1.5 |
| 8a | >500 | N/a | | 262 | | 30 |
| 9a | | 0.69 | | 2.32 | | 0.01 |
| 10 | >500 | n/a | >500 | n/a | >500 | n/a |
| Melphalan[b] | | 0.56 | | 0.21 | | 0.02 |

[a] The background shading reflect the potencies expressed as $IC_{50}$ values, namely black (<1 µM), dark grey (1-10 µM), grey (11-99 µM) and light grey (>100 µM).

TABLE 2

Cytotoxicity of representative compounds towards human tumor cell lines

| Comp | All cell lines | | Colon cancer cells, IC$_{50}$(μM) | | | | | | Leukemic cells, IC$_{50}$(μM) | | | |
|---|---|---|---|---|---|---|---|---|---|---|---|---|
| ID | IC$_{50}$(μM) | S.I.[a] | COLO 205 | HCT 116 | HCT 15 | KM 12 | SW 620 | HCC 2998 | K 562 | RPMI 8226 | HL 60 | SR |
| 1a[b] | 1.62 | 93.3 | 1.55 | 0.182 | 0.631 | 0.794 | 0.575 | 2.00 | 0.490 | 0.275 | 0.363 | 0.209 |
| 3b | 1.91 | 141 | 1.70 | 6.03 | 0.295 | 1.74 | 0.209 | 0.263 | 0.331 | 0.098 | 1.41 | 0.126 |
| 3d | 1.15 | 39.8 | 1.02 | 1.38 | 0.912 | 0.776 | 0.562 | 0.229 | 1.82 | 0.224 | 1.32 | 0.479 |
| 4a | <1.38 | >2455 | 2.63 | <0.01 | 1.17 | 1.74 | 1.35 | — | 0.043 | <0.01 | — | — |
| 5b | >11.5 | >66.1 | 15.8 | 47.9 | 49.0 | 19.1 | 3.55 | 1.58 | 4.37 | 0.759 | 20.4 | 2.29 |
| 5d | 1.38 | 93.3 | 6.92 | 1.58 | 1.07 | 0.148 | 0.339 | — | 0.589 | 0.123 | 0.933 | — |
| 6a | >2.63 | >457 | 22.9 | 0.339 | 1.45 | 0.129 | 0.191 | — | 0.158 | 0.123 | 0.562 | — |
| 6b | <0.562 | >2188 | — | 7.25 | 2.19 | 2.29 | 1.45 | <0.005 | 6.76 | 0.132 | 5.50 | — |
| 6d | <0.708 | >1738 | 1.15 | 2.45 | 0.832 | 1.12 | 1.02 | — | 0.275 | 0.115 | 1.10 | 0.245 |
| 7a | >41.7 | >4.47 | 20.4 | >50.1 | >50.1 | 43.7 | 30.2 | 28.2 | 43.7 | 17.4 | >50.1 | 38.0 |
| 7d | 7.76 | 166 | 8.91 | 14.1 | 9.33 | 9.33 | 10.5 | 6.17 | 1.35 | 1.26 | 11.8 | 22.9 |
| 5-Fluorouracil | >29.5 | >4365 | 3.39 | 2.04 | 6.61 | 7.94 | 18.6 | 5.75 | 126 | 3.55 | 85.1 | 60.3 |
| Melphalan | 26.9 | 118 | 66.1 | 30.2 | 36.3 | 43.7 | 38.9 | 41.7 | 43.7 | 66.1 | 2.04 | 1.86 |

[a]The letters SI refer to the selectivity index, i.e., the ratio of the IC$_{50}$ figures for the least and most sensitive cell lines to the compound.
[b]The hydrochloride salt of 1a was used in this assay

TABLE 3

MDR-reversing properties and cytotoxicity of the compounds in series 1 and 3-7

| Compound | FAR value[a] | | CC$_{50}$(μM)[b] | | | | | | | |
|---|---|---|---|---|---|---|---|---|---|---|
| ID | 4 μg/ml | 40 μg/ml | HSC-2 | HSC-4 | HL-60 | ave[c] | HGF | HPC | HPLF | SI[d] |
| 1a | 1.58 | 2.00 | 2.2 | 4.4 | 1.5 | 2.7 | 20 | 38 | 24 | 10 |
| 1d | 3.26 | 4.03 | 3.9 | 9.3 | 4.5 | 5.9 | 150 | 200 | 170 | 29 |
| 1b | 1.25 | 0.91 | 18 | 20 | 22 | 20 | 69 | 130 | 56 | 4.3 |
| 1c | 1.04 | 0.80 | 0.90 | 6.1 | 3.6 | 3.5 | 13 | 88 | 39 | 13 |
| 3a | 45.5 | 51.6 | 3.8 | 2.1 | 1.0 | 2.3 | 3.6 | 13 | 8.9 | 3.7 |
| 3d | 83.7 | —[e] | 1.4 | 2.1 | 0.85 | 1.5 | 7.9 | 7.2 | 3.4 | 4.3 |
| 3b | 98.0 | 98.9 | 2.3 | 1.8 | 1.7 | 1.9 | 23 | 11 | 4.3 | 6.6 |
| 3c | 63.0 | 3.23 | 0.93 | 0.71 | 0.31 | 0.7 | 7.0 | 5.2 | 5.9 | 9.3 |
| 4a | 49.5 | 23.8 | 3.1 | 2.0 | 0.61 | 1.9 | 4.2 | 12 | 6.0 | 3.9 |
| 4d | 106 | 66.6 | 2.2 | 2.3 | 0.79 | 1.8 | 3.6 | 9.3 | 4.6 | 3.3 |
| 4b | 118 | 99.7 | 160 | 34 | 46 | 80 | 230 | >400 | >400 | >4.3 |
| 4c | 77.5 | 14.1 | 0.98 | 1.1 | 0.26 | 0.8 | 5.0 | 4.5 | 5.9 | 6.6 |
| 5a | 123 | 136 | 3.0 | 2.5 | 1.4 | 2.3 | 4.6 | 12 | 7.4 | 3.5 |
| 5d | 179 | 146 | 2.9 | 4.1 | 2.3 | 3.1 | 6.0 | 15 | 5.5 | 2.9 |
| 5b | 157 | 133 | 110 | 48 | 63 | 74 | >400 | >400 | 340 | >5.2 |
| 5c | 145 | 51.5 | 0.86 | 0.90 | 0.29 | 0.7 | 8.0 | 3.9 | 4.9 | 8.2 |
| 6a | 48.5 | 63.3 | 2.4 | 2.4 | 1.2 | 2.0 | 83 | 95 | 30 | 35 |
| 6d | 95.8 | 124 | 1.6 | 2.0 | 1.2 | 1.6 | 10 | 49 | 12 | 15 |
| 6b | 76.0 | 6.88 | 71 | 18 | 36 | 42 | 400 | >400 | 360 | >9.3 |
| 6c | 63.3 | 10.9 | 0.76 | 0.74 | 0.35 | 0.6 | 12 | 8.2 | 9.3 | 16 |
| 7a | 1.37 | 1.05 | 130 | 82 | 82 | 98 | 160 | 170 | 79 | 1.4 |
| 7d | 1.93 | 114 | 17 | 17 | 16 | 17 | 34 | 29 | 8.3 | 1.4 |
| 7b | 1.21 | 1.85 | >400 | 220 | 64 | 228 | >400 | >400 | 9.4 | ~1.2 |
| 7c | 1.03 | 1.22 | 67 | 61 | 29 | 52 | 93 | 13 | 1.5 | |
| Melphalan | — | — | 35 | 81 | 6 | 40.7 | >200 | >200 | >200 | >4.9 |

[a]The fluorescence activity ratio (FAR) values are the ratios of the fluorescent intensities of rhodamine 123 in treated and untreated murine L-5178 cells. A reference drug verapamil had a FAR value of 5.61 using a concentration of 10 μg/ml.
[b]The CC$_{50}$ values are the concentration of the compounds which kill 50% of the cells and are the average of two independent determinations.
[c]These figures are the average CC$_{50}$ figures for the HSC-2, HSC-4 and HL-60 malignant cells.
[d]The letters SI refer to the selectivity index which was computed by dividing the average CC$_{50}$ figures of the HGF, HPC and HPLF cells by the average CC$_{50}$ values of the HSC-2, HSC-4 and HL-60 neoplasms. [e] A concentration of 40 μg/ml of 3d was toxic to the cells.

What is claimed is:

1. A 4-piperidone compound represented by structural formula (I):

wherein
R¹ and R² independently represent a substituted or unsubstituted phenyl, said substituted phenyl having a single substituent at the 2, 3, or 4 position or having multiple independent substituents at the 2,3; 2,4; 2,5; 2,6; 3,4; 3,5; 3,6; 4,6; 2,3,4; 2,4,6; or 3,4,5 positions, said substituents being selected from the group consisting of halogen, alkoxy, alkyl, phenyl, nitro, and phosphonate groups;

R³ and R⁴ independently represent H, alkyl, hydroxyalkyl, or carboxylate ester, wherein each R³ and each R⁴ may be the same or different;

n represents an integer from 1 to 4 and indicates the number of Y(CH$_2$)$_o$Z substituents on the benzene ring;

o represent an integer from 1 to 4;

X represents (CH$_2$)$_r$, CO, COO, where r represents an integer from 1 to 4;

Y represents O, S, NH, N(alkyl), N(aryl), or (CH$_2$)$_s$, where s represents an integer from 1 to 4; and Z represents N(alkyl)$_2$, NH(alkyl), N(aryl)$_2$, NH(aryl), +N(alkyl)$_3$, or where B represents O, S, CH$_2$, NH, N-alkyl, or N-aryl, p represents 1 or 2, and q represents 2 or 3;

or a pharmaceutically acceptable salt thereof.

2. The compound of claim 1, wherein Y(CH$_2$)$_o$Z is located at the 2, 3, or 4 position of the benzene ring.

3. The compound of claim 2, wherein Y(CH$_2$)$_o$Z is located at the 4 position of the benzene ring.

4. The compound of claim 1, wherein R³ and R⁴ are hydrogen.

5. The compound of claim 1, wherein Y(CH$_2$)$_o$Z is located at the 4 position of the benzene ring, R³ and R⁴ are hydrogen, X is CO, n is 1, Y is O, and o is 2.

6. The compound of claim 1, wherein Y(CH$_2$)$_o$Z is located at the 4 position of the benzene ring, R³ and R⁴ are hydrogen, X is CO, n is 1, Y is O, and o is 1, 3 or 4.

7. A method of preparing the compound of claim 1, comprising the step of reacting a compound of formula (IV)

with a compound of formula T-A' (V), in the presence of a base, where T represents a halogen, and A' represents 8. The method of claim 7, wherein the solvent is a polar aprotic solvent or a halogenated hydrocarbon solvent.

9. The method of claim 8, wherein the polar aprotic solvent is tetrahydrofuran or acetonitrile.

10. The method of claim 8, wherein the halogenated hydrocarbon solvent is chloroform, dichloromethane, or 1,2-dichloroethane.

11. The compound of claim 1, wherein X is COO.

12. The compound of claim 1, wherein X is CO.

13. The compound of claim 1, wherein Y is O.

14. The compound of claim 1, wherein o is 2.

15. The compound of claim 1, wherein X is CO, Y is O, and o is 2.

16. A 4-piperidone compound selected from the group consisting of:
1-[4-(2-Dimethylaminoethoxy)phenylcarbonyl]-3,5-bis(phenylmethylene)-4-piperidone hydrochloride (3a);
3,5-bis(4-Chlorophenylmethylene)-1-[4-(2-dimethylaminoethoxy)phenyl-carbonyl]-4-piperidone hydrochloride hemihydrate (3b);
1-[4-(2-Dimethylaminoethoxy)phenylcarbonyl]-3,5-bis(4-nitrophenylmethylene)-4-piperidone hydrochloride hemihydrate (3c);
1-[4-(2-Dimethylaminoethoxy)phenylcarbonyl]-3,5-bis(4-methylphenyl-methylene)-4-piperidone hydrochloride hemihydrate (3d);
1-[4-(2-Diethylaminoethoxy)phenylcarbonyl]-3,5-bis(phenylmethylene)-4-piperidone hydrochloride hemihydrate (4a);
3,5-bis(4-Chlorophenylmethylene)-1-[4-(2-diethylaminoethoxy)phenylcarbonyl]-4-piperidone hydrochloride (4b);
1-[4-(2-Diethylaminoethoxy)phenylcarbonyl]-3,5-bis(4-nitrophenylmethylene)-4-piperidone hydrochloride (4c);
1-[4-(2-Diethylaminoethoxy)phenylcarbonyl]-3,5-bis(4-methylphenylmethylene)-4-piperidone hydrochloride (4d);
1-[4-{2-(1-Piperidinyl)ethoxy}phenylcarbonyl]-3,5-bis(phenylmethylene)-4-piperidone hydrochloride hemihydrate (5a);

3,5-bis(4-Chlorophenylmethylene)-1-[4-{2-(1-piperidinyl)ethoxy}phenylcarbonyl]-4-piperidone hydrochloride (5b);

3,5-bis(4-Nitrophenylmethylene)-1-[4-{2-(1-piperidinyl)ethoxy}phenylcarbonyl]-4-piperidone hydrochloride 1.5 hydrate (5c);

3,5-bis(4-Methylphenylmethylene)-1-[4-{1-piperidinyl)ethoxy}phenylcarbonyl]-4-piperidone hydrochloride hemihydrate (5d);

1-[4-{2-(4-Morpholinyl)ethoxy}phenylcarbonyl]-3,5-bis(phenylmethylene)-4-piperidone hydrochloride hemihydrate (6a);

3,5-bis(4-Chlorophenylmethylene)-1-[4-{2-(4-morpholinyl)ethoxy}phenylcarbonyl]-4-piperidone hydrochloride (6b);

1-[4-{2-(4-Morpholinyl)ethoxy}phenylcarbonyl]-3,5-bis(4-nitrophenylmethylene)-4-piperidone hydrochloride hemihydrate (6c); and 3,5-bis(4-Methylphenylmethylene)-1-[4-{2-(4-morpholinyl)ethoxy}phenylcarbonyl]-4-piperidone hydrochloride hemihydrate (6d).

\* \* \* \* \*